United States Patent [19]
Persichetti

[11] Patent Number: 6,079,977
[45] Date of Patent: Jun. 27, 2000

[54] DENTAL IMPRESSION TRAY

[76] Inventor: Joseph A. Persichetti, 752 Holland Rd., Holland, Pa. 18966

[21] Appl. No.: 09/261,183

[22] Filed: Mar. 3, 1999

[51] Int. Cl.⁷ ...................................................... A61C 9/00
[52] U.S. Cl. .................................. 433/37; 433/41; 433/42
[58] Field of Search ................... 433/37, 41, 42, 433/43, 44, 45, 46, 47, 48, 38, 39

[56] References Cited

U.S. PATENT DOCUMENTS

| | | | |
|---|---|---|---|
| 1,629,177 | 5/1927 | Sahr | 433/41 |
| 3,207,153 | 9/1965 | Goldstein | 433/37 |
| 5,064,371 | 11/1991 | Smeltzer | 433/37 |
| 5,336,086 | 8/1994 | Simmen et al. | 433/37 |
| 5,478,235 | 12/1995 | Schuldt et al. | 433/37 |
| 5,752,826 | 5/1998 | Andreiko | 433/37 |
| 5,769,633 | 6/1998 | Jacobs et al. | 433/48 |
| 5,772,432 | 6/1998 | Jordan et al. | 433/37 |

FOREIGN PATENT DOCUMENTS 3410487  9/1985  Germany .................................. 433/37

*Primary Examiner*—John J. Wilson
*Assistant Examiner*—Robyn Kieu Doan
*Attorney, Agent, or Firm*—Gregory J. Gore

[57] ABSTRACT

A dental impression tray includes venting in the palatal area of the tray that permits excess impression material to be expelled downward and forward as the impression material and tray are forced upward against the patient's teeth when the impression is taken. At least one vent is located along the apex of the palatal shelf portion of the tray. A pressure plate is also employed which lies substantially in the plane of the base of the tray near the back of the tray. The pressure plate provides a reduced pressure against the impression material and also provides a convenient place in the center of the dental tray for the clinician to apply upward finger pressure to control the positioning and pressure of the tray against the patient's teeth as it is applied.

3 Claims, 1 Drawing Sheet

DENTAL IMPRESSION TRAY

FIELD OF THE INVENTION

This invention relates to a dental impression tray holding moldable material that is placed in the tray to make an impression of teeth and areas of a patient's oral cavity. More specifically, it relates to an impression tray with means to facilitate the expulsion of excess impression material while taking an upper arch dental impression.

BACKGROUND OF THE INVENTION

The use of trays for holding impression material to make impressions of teeth and other areas of a patient's oral cavity are well known. During the impression-taking process, trays are filled with dental impression material which is then impressed onto several of the patient's teeth or against the entire upper or lower dental arch. To ensure a complete impression, it is essential that an excessive amount of impression material be used. While the tray and impression material are held in place, the material cures, and after curing the tray and material are removed from the mouth as a unit. The resulting impression is then used as a casting mold to form a model of the patient's teeth.

Trays used for taking impressions of the upper dental arch generally include a "U"-shaped trough to conform to the natural configuration of the dental arch. An area in the middle of the "U" generally includes an upward-extending pocket beneath an arched shelf to conform to the general shape of the patient's palate. This configuration is, in general, universally employed in the prior art.

A problem exists, however, in such a tightly fitting upper arch impression tray because the expulsion of the essential excess material is extremely uncomfortable for the patient. With the prior art configuration described above, the excess impression material is expelled backward into the throat area of the patient causing a gag reflex reaction which is extremely uncomfortable. There is, therefore, a need in the art for a new and improved impression tray which provides for the expulsion of excess impression material without gagging the patient.

SUMMARY OF THE INVENTION

This invention has been devised by the applicant to meet the above-stated need in the art to provide an upper arch dental impression tray which provides enhanced patient comfort. This is achieved in the present invention by the provision of a vented palatal section and the inclusion of a trans-palatal pressure plate extending across the base of the dental tray at the rear. In other respects, the dental impression tray of the present invention is similar to those generally known in the art.

In normal practice, a tray filled with fresh impression material is first pushed upward against the front teeth with the rear of the tray held at the downward angle. The tray is then rotated so that the rear of the tray moves upward against the rear portion of the oral cavity until the base of the dental tray is parallel with the occlusal plane of the upper dental arch. Because the impression material is applied in this way, the above mentioned tendency for excess dental impression material to be expelled backward into the patient's throat results.

With the present invention, however, venting in the palatal area permits the excess impression material to be expelled downward as the impression material and tray are forced upward against the patient's teeth. As the rear portion of the tray is forced upward, the excess impression material is not trapped between the upwardly extending palatal area of the tray but rather is expelled downward through this central vent and thus is not forced backward. This prevents being forced into the patient's throat causing the unwanted gag reflex. The transpalatal force plate at the rear of the impression tray provides sufficient support for the excess impression material so that there is maintained a pressure against the excess impression material that, while reduced, is sufficient to provide an adequate impression of the soft tissue in the area of the patient's palate. Since the dental trays are inserted and applied manually, the pressure plate also provides a convenient place at the rear and in the center of the dental tray for the clinician to apply upward finger pressure to control the positioning and pressure of the tray against the patient's teeth as it is applied.

More specifically, the applicant has invented a dental impression tray for use with a settable impression material during the taking of a dental impression, comprising: a generally U-shaped trough having a substantially planar base and an L-shaped lateral cross-section. A pair of legs of the trough extend rearwardly terminating at a rearmost end of the tray, the legs being separated by a transpalatal distance at their end. The tray further includes an upwardly extending arch palatal shelf between the legs. The shelf includes at least one vent located along the apex of the shelf for forwardly transmitting the expulsion of excess impression material as the impression is taken. The sides of the trough include inner and outer opposing walls extending vertically from a planar base of the tray. The inner wall of the trough extends to a height from the base less than the outer wall. The invention may further include a pressure plate lying substantially in the plane of the base and extending between the trough legs adjacent to the rearmost end of the tray.

It is therefore the primary object of the present invention to provide a dental impression tray with means to afford enhanced patient comfort. It is a further object of the present invention to provide increased patient comfort by incorporating a central vent into the palatal area of an upper arch dental impression tray to prevent excess impression material from being expelled backward during the impression-taking process. Further objects and advantages of the present invention will become apparent to those of ordinary skill in the art from reference to the following drawings and detailed description of the preferred embodiment.

DESCRIPTION OF THE PREFERRED EMBODIMENT

Figure 1:
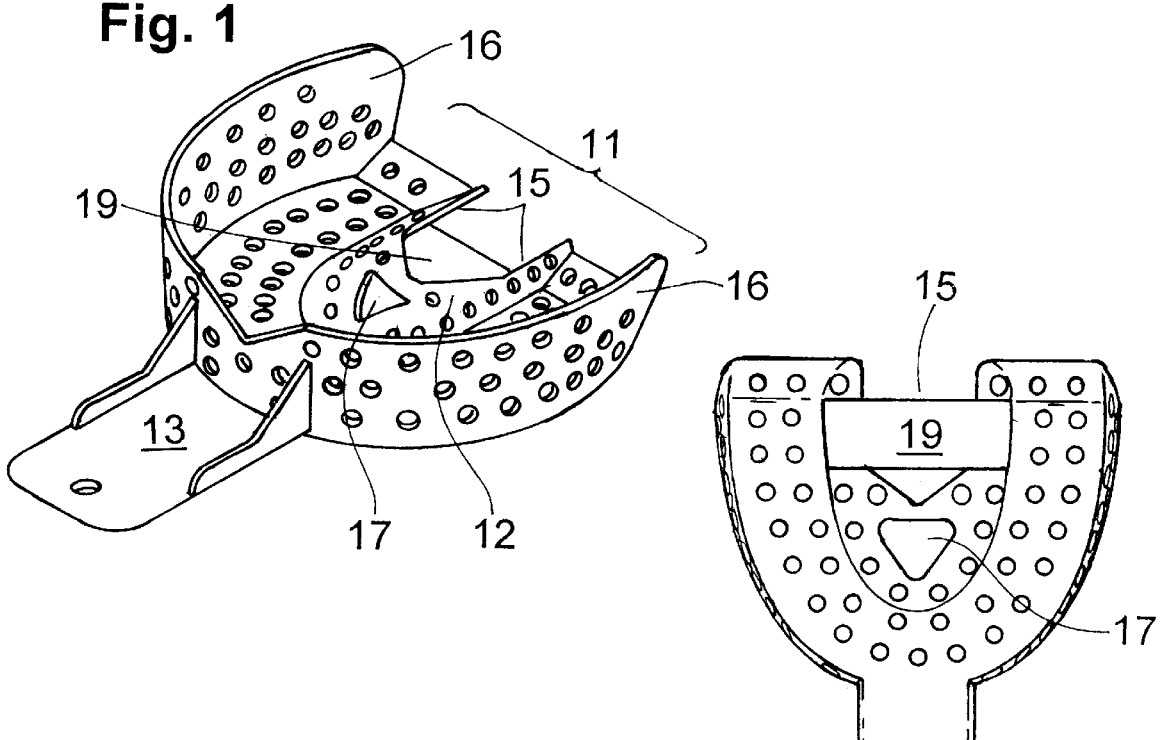
FIG. 1 is a top right front isometric view of the present invention.

FIG. 1 depicts an embodiment of the present invention which shows its unique construction. Being an upper arch dental impression tray, it has the usual configuration and characteristics including a curved dental impression trough 11 which includes two legs 16 which terminate at a rearmost end of the tray, generally shaped to conform to the natural shape of the patient's dental arch. The present tray is of the type commonly used which includes a multiplicity of small perforations throughout its surface to increase the adherence of the impression material. A handle at the front 13 provides a convenient point for manual grasping by the clinician. The dental impression trough has a generally L-shaped lateral cross-section and includes an upward projecting central palatal shelf 12 which extends between the inner side edges of the troughs. The troughs are further described as having rearwardly extending legs which terminate at a rearmost end of the tray opposite handle 13. The trough is created by opposing inner and outer walls with the outer wall being vertically higher than the inner wall, which is formed by the raised palatal shelf forming the L-shaped lateral cross-section. One unique aspect of the present invention, however, is the inclusion of vent cutouts 15 and 17. These vents include a large rear cut-out 15 and a smaller triangular-shaped vent 17 toward the front. As will be more fully described below, the present invention also includes a unique trans-palatal pressure plate 19 which extends between the inner side edges of the impression trough at the rear. In the preferred embodiment, the impression plate is flat and extends in the plane of the base of the dental impression tray.

Figure 2:
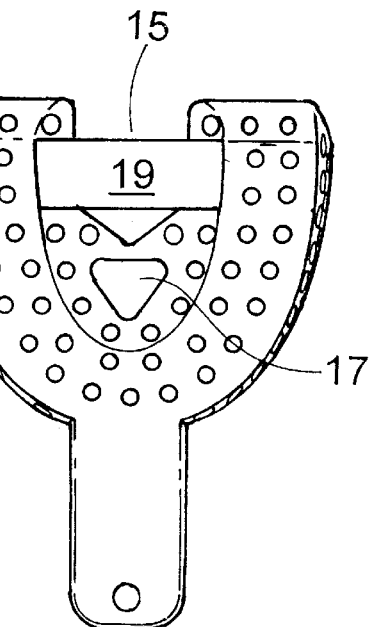
FIG. 2 is a bottom view of the invention shown in FIG. 1.

Referring now to FIG. 2, a bottom view of the present invention shows more clearly the location of the pressure plate 19 which serves at least two functions. First, it provides support for excess impression material between the top of the pressure plate and the patient's palate so that sufficient force is provided against the impression material to permit an accurate impression of the soft tissue of the patient's palate. The combination of the pressure plate structure with the large vent opening directly above it provides a downward and forwardly projecting duct for passage of excess impression material. The force plate also provides a convenient place for the clinician to apply the necessary manual pressure against the impression tray when forcing the tray upward in the patient's oral cavity. This figure also depicts a forward vent 17 which provides an additional downward discharge exit for excess impression material in the front of the palatal area. The inclusion of these vents permits the excess impression material to be expelled primarily downward during the impression-taking process and not backward. Thus, the excess material is not expelled in the direction of the patient's throat, thus eliminating the uncomfortable gag reflex.

Figure 3:
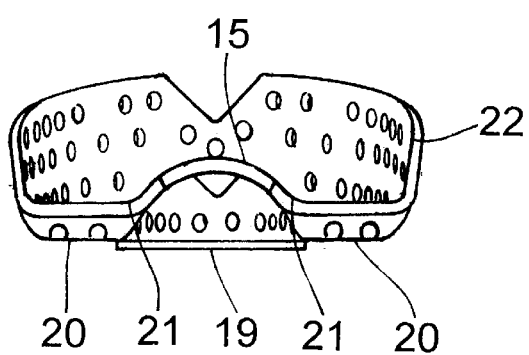
FIG. 3 is a rear view of the invention shown in FIGS. 1 and 2.

Referring now to FIG. 3, a rear view of the present invention is shown. As in the case with the prior art upper dental arch impression trays, the central palatal surface in the center extends upwardly below the height of the side edges of the dental impression trough, however, the uppermost areas of the palatal impression surface along its apex have been cut away to provide the above-described vents. The L-shaped lateral cross-section of the trough can be clearly seen in this view. The outer walls 22, together with the raised portions 21 of the palatal shelf, form the inner surfaces of tray which receive the impression material. Force plate 19 as clearly shown in this figure, resides in the plane of the dental impression tray base 20 and extends centrally from the inner side surfaces of the legs of the trough at the rear.

While the description of the preferred embodiment provided above specifically discloses the preferred construction of the present invention, it should be understood that there are many modifications and adaptations which may be employed while not departing from the scope and spirit of the invention as claimed. For example, the novel vents at the apex of the palatal area of the tray may vary in size, location and geometry. Similarly, the pressure plate may be employed with or without the venting and represents a separate and novel feature of the applicant's invention. Similarly, the location, size and shape of the force plate may be varied in size and specific location without significantly departing from its functionality. For example the force plate, while shown as a flat planer element, may be slightly curved upwardly and angled downward in the front to facilitate the frontal discharge of expelled excess impression material. Also, the particular geometry as disclosed in the preferred embodiment may vary according to the specific type of dental impression material used. With the foregoing in mind, the applicant's invention should be limited only by the following claims and their legal equivalents.

What is claimed is:

1. A dental impression tray for use with a settable impression material during the taking of a dental impression, comprising:

a generally U-shaped trough having a substantially planar base and an L-shaped lateral cross-section;

a pair of rearwardly extending legs of said trough terminating at a rearmost end of said tray, said legs being separated by a transpalatal distance which is greatest at said rearmost end of said legs;

an upwardly extending palatal shelf extending between said legs; and a pressure plate lying in a plane of said base and extending between said legs adjacent said rearmost end of said tray.

2. The dental impression tray of claim 1, further described in that said trough is comprised of inner and outer walls extending vertically from said planar base and wherein said inner wall extends to a height from said base less than said outer wall.

3. The dental impression tray of claim 1, further described in that said trough is comprised of an inner and outer wall extending vertically from said planar base and wherein said inner wall extends to a height from said base greater than said outer wall.

* * * * *